US010736831B2

(12) United States Patent
Kinscherf et al.

(10) Patent No.: US 10,736,831 B2
(45) Date of Patent: Aug. 11, 2020

(54) ORAL CARE COMPOSITIONS

(71) Applicant: Colgate-Palmolive Company, New York, NY (US)

(72) Inventors: Kevin Mark Kinscherf, Middletown, NJ (US); Lyndsay Schaeffer-Korbylo, Flemington, NJ (US); Gregory Szewczyk, Flemington, NJ (US); Carl Myers, Wayne, NJ (US); Harsh Mahendra Trivedi, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/745,484

(22) PCT Filed: Jul. 17, 2015

(86) PCT No.: PCT/US2015/040927
§ 371 (c)(1),
(2) Date: Jan. 17, 2018

(87) PCT Pub. No.: WO2017/014723
PCT Pub. Date: Jan. 26, 2017

(65) Prior Publication Data
US 2018/0207076 A1   Jul. 26, 2018

(51) Int. Cl.
| *A61K 8/58* | (2006.01) |
| *A61K 8/27* | (2006.01) |
| *A61K 8/46* | (2006.01) |
| *A61Q 11/00* | (2006.01) |
| *A61K 47/34* | (2017.01) |
| *A61K 45/06* | (2006.01) |
| *A61K 9/08* | (2006.01) |
| *A61K 8/30* | (2006.01) |
| *A61K 33/30* | (2006.01) |
| *A61K 33/00* | (2006.01) |
| *A61P 1/02* | (2006.01) |
| *A61K 8/21* | (2006.01) |
| *A61K 8/25* | (2006.01) |

(52) U.S. Cl.
CPC .............. *A61K 8/58* (2013.01); *A61K 8/21* (2013.01); *A61K 8/25* (2013.01); *A61K 8/27* (2013.01); *A61K 8/30* (2013.01); *A61K 8/463* (2013.01); *A61K 9/08* (2013.01); *A61K 33/00* (2013.01); *A61K 33/30* (2013.01); *A61K 45/06* (2013.01); *A61K 47/34* (2013.01); *A61P 1/02* (2018.01); *A61Q 11/00* (2013.01); *A61K 2800/58* (2013.01)

(58) Field of Classification Search
None
See application file for complete search history.

(56) References Cited

U.S. PATENT DOCUMENTS

| 4,092,272 A | 5/1978 | Nishimura et al. |
| 5,635,466 A | 6/1997 | Burdon et al. |
| 6,174,522 B1 | 1/2001 | Baravetto et al. |
| 8,236,357 B2 | 8/2012 | Bobbert |
| 2006/0099152 A1 | 5/2006 | Day et al. |
| 2015/0196474 A1 | 7/2015 | Baco |
| 2015/0335539 A1 | 11/2015 | Prencipe et al. |

FOREIGN PATENT DOCUMENTS

| DE | 102014223535 | 7/2015 |
| EP | 1074247 | 9/2006 |
| EP | 2399576 | 1/2018 |
| FR | 2992859 | 1/2014 |
| WO | WO 2002/45678 | 6/2002 |
| WO | WO 2008/071746 | 6/2008 |
| WO | WO 2012/163928 | 12/2012 |

OTHER PUBLICATIONS

International Search Report and Written Opinion of the International Searching Authority in International Application No. PCT/US2015/040927, dated Dec. 21, 2015.
Zschimmer & Schwarz Italiana S.p.A., 2003, "Zetesol ZN An alkyl ether sulfate with surprising applications," http://www.erwebhosting.it/zsi/repository/Zetesol%20ZN%20-%20An%20alkyl%20ether%20sulfate%20with%20suprising%20application.pdf.

*Primary Examiner* — Nannette Holloman

(57) ABSTRACT

An oral care composition comprising a surfactant having formula $[R(OC_2H_4)_xOSO_3]_2M$ wherein R is a saturated or unsaturated alkyl group with an alkyl chain length of 8 to 30 carbon atoms; x is from 0 to 10; and M is a divalent metal cation selected from zinc cations, copper cations and stannous cations is provided.

9 Claims, 1 Drawing Sheet

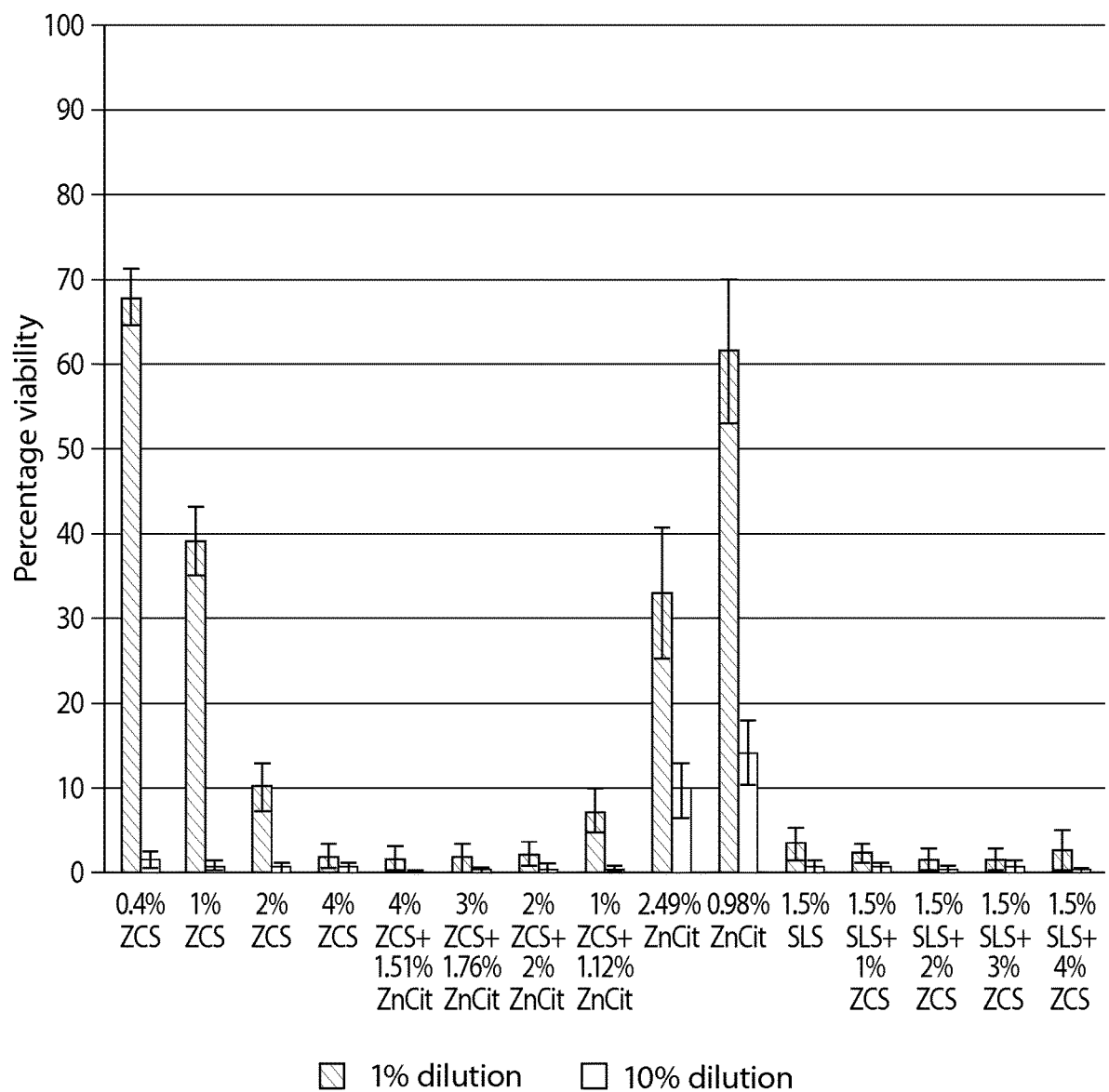

ORAL CARE COMPOSITIONS

BACKGROUND

The present invention relates to oral care compositions comprising metal cations, and in particular to oral care compositions comprising zinc, copper and stannous cations. The present invention also relates to the use of such compositions for oral care, and to methods using such compositions.

Metal cations such as zinc, copper and stannous can be used in oral care compositions to provide oral care benefits such as antibacterial and bacteriostatic activity, and to fight plaque and gingivitis. However, oral care compositions comprising metal cations can suffer from negative taste problems. In particular, certain consumers may find oral care compositions comprising metal cations to be astringent.

It would therefore be desirable to be able to formulate oral care compositions comprising beneficial metal cations that do not suffer from excessive taste problems.

BRIEF SUMMARY

It has now surprisingly been discovered that incorporating metal cations in the form of an alkyl sulfate surfactant into oral care compositions can provide therapeutically useful levels of the metal component at lower incorporation levels than traditional metal compounds. Thus, any negative taste implications are reduced.

According to a first aspect of the invention, there is provided an oral care composition comprising a surfactant having formula $$[R(OC_2H_4)_xOSO_3]_2M$$

wherein
R is a saturated or unsaturated alkyl group with an alkyl chain length of 8 to 30 carbon atoms;
x is from 0 to 10; and
M is a divalent metal cation selected from zinc cations, copper cations and stannous cations.

Optionally the surfactant is present in an amount of 0.10 weight % to 10.0 weight % based on the total weight of the composition.

Optionally R is a saturated or unsaturated alkyl group with 10 to 18 carbon atoms. Further optionally R is a saturated alkyl group with 10 to 18 carbon atoms.

Optionally x is from 1 to 4.

Optionally R is a saturated alkyl group with 11 carbon atones and x is 3.

Optionally the oral care composition comprises a mixture of surfactant compounds, the surfactant compounds having a mean alkyl chain length of 10 to 16 carbon atoms.

Optionally the oral care composition comprises a mixture of surfactant compounds having a mean value for x of from 1 to 4. Further optionally the oral care composition comprises a mixture of surfactant compounds having a mean alkyl chain length of 10 to 16 carbon atoms and a mean value for x of from 1 to 4.

Optionally M is a Zn(II) cation.

Optionally the oral care composition comprises from 0.01 weight % to 1.0 weight % M based on the total weight of the composition. Further optionally the oral care composition comprises 0.01 weight % to 0.80 weight % M, based on the total weight of the composition. Further optionally the oral care composition comprises from 0.01 weight % to 0.75 weight % M, from 0.01 weight % to 0.60 weight % M, from 0.01 weight % to 0.50 weight % M or from 0.02 weight % to 0.20 weight % M, based on the total weight of the composition.

Optionally the oral care composition comprises zinc coco sulfate or zinc coceth sulfate. Further optionally the oral care composition comprises zinc coceth sulfate.

Optionally the oral care composition further comprises an orally acceptable vehicle.

Optionally the composition is a dentifrice or mouthwash.

Optionally the composition further comprises a fluoride ion source.

Optionally the composition further comprises a zinc ion source selected from zinc citrate, zinc sulfate, zinc oxide, zinc fluoride, zinc chloride, zinc lactate, zinc gluconate, zinc malate, zinc tartrate, zinc carbonate, zinc phosphate and mixtures thereof.

Optionally the composition further comprises a non-zinc containing anionic surfactant. Further optionally the composition further comprises sodium lauryl sulfate.

Optionally the oral care composition further comprises silica.

Optionally the oral care composition further comprises a polyphosphate.

Optionally the composition is a dentifrice comprising 0.10 weight % to 10.0 weight % zinc coceth sulfate; and 0.05 weight % to 5.0 weight % sodium lauryl sulfate.

According to a further aspect of the present invention there is provided a method of
(i) treating gingivitis and/or periodontitis,
(ii) reducing dental plaque accumulation and/or
(iii) reducing bacteria in the oral cavity of a subject,
said method comprising applying a composition according to any preceding claim to the oral cavity of a subject.

According to a further aspect of the present invention there is also provided compositions for use in a method of
(i) treating gingivitis and/or periodontitis,
(ii) reducing dental plaque accumulation and/or
(iii) reducing bacteria in the oral cavity of a subject,
said method comprising applying the composition to the oral cavity of a subject.

According to a further aspect of the present invention there is also provided use of compositions to
(i) treat gingivitis and/or periodontitis,
(ii) reduce dental plaque accumulation and/or
(iii) reduce bacteria in the oral cavity of a subject.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 demonstrates the effect of compositions according to the invention on bacterial metabolism/viability.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. in the event of a conflict in a definition in the present disclosure and that of a cited reference, the present disclosure controls.

The oral care compositions of the present invention comprise an alkyl ether sulfate surfactant having formula

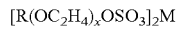

wherein
R is a saturated or unsaturated alkyl group with an alkyl chain length of 8 to 30 carbon atoms;
x is from 0 to 10; and
M is a divalent metal cation selected from zinc cations, copper cations and stannous cations.

In certain embodiments, the oral care compositions of the present invention comprise a mixture of surfactant molecules each having formula

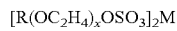

wherein
R is a saturated or unsaturated alkyl group with an alkyl chain length of 8 to 30 carbon atoms;
x is from 0 to 10; and
M is a divalent metal cation selected from zinc cations, copper cations and stannous cations.

The anionic surfactants used in the compositions of the invention comprise an anionic sulfate group at the head and a hydrocarbon tail. Alkyl ether sulfates (i.e. compounds of formula $[R(OC_2H_4)_xOSO_3]_2M$ in which x is greater than 1) are typically prepared as condensation products of ethylene oxide and monohydric alcohols having from about 8 to about 30 carbon atoms. The alcohols can be derived from fats such as coconut oil, palm oil, tallow, or can be synthetic alcohols. In certain embodiments, the surfactants used in the compositions of the present invention (e.g. alkyl ether sulfates) are prepared from straight chain alcohols derived from coconut oil and palm oil. In certain embodiments, the compositions of the present invention comprise alkyl ether sulfates prepared from straight chain alcohols derived from coconut oil. Coconut oil comprises a mixture of fatty acids, and can comprise a mixture of caprylic saturated $C_8$ fatty acid, decanoic saturated $C_{10}$ fatty acid, lauric saturated $C_{12}$ fatty acid, myristic saturated $C_{14}$ fatty acid, palmitic saturated $C_{16}$ fatty acid and oleic monounsaturated $C_{18:1}$ fatty acid. The alcohols can be reacted with 1 to about 10 moles of ethylene oxide and the resulting products sulfated and neutralized. The surfactant obtained by such a method can comprise a mixture of components with different R groups (alkyl chain length) and different degrees of ethoxylation (x).

The oral care compositions of the invention can comprise a mixture of individual surfactant compounds, such as for example a mixture of alkyl ether sulfate compounds. In certain embodiments the composition comprises a mixture of compounds wherein the mixture has an average alkyl chain length (R) of from 8 to 16 carbon atoms, for example from 12 to 16 carbon atoms. The alkyl chain R may be saturated or unsaturated, straight chain or branched. In certain embodiments the composition comprises a mixture of alkyl ether sulfate compounds having an average alkyl chain length of from about 12 to about 16 carbon atoms and an average degree of ethoxylation of from about 1 to about 4 moles of ethylene oxide i.e. an average value for x of from 1 to 4. In certain embodiments the composition comprises a surfactant in which R is a straight unbranched alkyl chain having 11 carbon atoms and x is 3. In certain embodiments the composition may comprise a mixture of compounds, the mixture having from about 0 to about 20 weight % compounds having alkyl chain length (R) of from 12 to 13 carbon atoms; from about 60 to about 100 weight % compounds having alkyl chain length (R) of from 14 to 16 carbon atoms; 0 to about 20 weight % compounds having alkyl chain length (R) of from 17 to 19 carbon atoms; from about 45 weight % to about 90 weight % compounds having x from about 1 to about 4; from about 10 weight % to about 25 weight % compounds having x from 5 to 8 and from about 0.1 weight % to about 15 weight % compounds having x from 9 to 10.

The surfactants of the present invention comprise a metal cation which can provide oral care benefits. Certain metal ions are known to provide therapeutic oral care benefits including antibacterial activity, plaque reduction and/or reduction of oral malodor (halitosis). However, the incorporation of metal salts into oral care products can lead to unpleasant astringent organoleptic sensations such as a dry, puckering feeling in the oral cavity. By incorporating beneficial metal cations into oral care compositions in the form of an alkyl ether sulfate surfactant, the present inventors have discovered that compositions can be formulated that can provide a high level of antibacterial efficacy, at lower levels of total metal. Thus the unpleasant astringent taste of the metal in the composition is minimized without compromising on the oral care benefits obtained.

In certain embodiments, M is a divalent stannous (tin), copper or zinc cation. In certain embodiments, M is a zinc(II) cation. In certain embodiments the compositions of the invention comprise zinc alkyl ether sulfate surfactants. In certain embodiments the oral care compositions of the invention comprise a zinc alkyl ether sulfate surfactant, such as for example a zinc alkyl ether sulfate surfactant based on coconut oil. In certain embodiments the compositions of the invention comprise zinc coco sulfate. In certain embodiments the compositions of the invention comprise zinc coceth sulfate. A surfactant suitable for use in the compositions of the present invention is zinc coceth sulfate sold by Zschimmer & Schartz under the name ZETESOL ZN. In certain embodiments, zinc coceth sulfate is incorporated into the compositions as a 25% solution i.e. as a solution comprising 25% active material.

In certain embodiments the alkyl ether sulfate is present in the oral care composition in an amount of from 0.10 weight % to 10.0 weight % active material based on the total weight of the composition. In certain embodiments the alkyl ether sulfate is present in the oral care composition in an amount of from 0.20 weight % to 8.0 weight % active material based on the total weight of the composition, from 0.20 weight % to 6.0 weight % active material based on the total weight of the composition, from 0.20 weight % to 5.0 weight % active material based on the total weight of the composition, from 0.50 weight % to 10.0 weight % active material based on the total weight of the composition, from 0.50 weight % to 8.0 weight % active material based on the total weight of the composition, from 1.0 weight % to 8.0 weight % active material based on the total weight of the composition or from 1.0 weight % to 5.0 weight % active material based on the total weight of the composition. For example, in certain embodiments, the oral care composition may comprise from 0.10 weight % to 10.0 weight % zinc coceth sulfate, from 0.20 weight % to 8.0 weight % zinc coceth sulfate, from 0.20 weight % to 6.0 weight % zinc coceth sulfate, from 0.20 weight % to 5.0 weight % zinc coceth sulfate, from 0.50 weight % to 10.0 weight % zinc coceth sulfate, from 0.50 weight % to 8.0 weight % zinc coceth sulfate, from 1.0 weight % to 8.0 weight % zinc coceth sulfate or from 11.0 weight % to 5.0 weight % zinc coceth sulfate based on the total weight of the composition.

In certain embodiments the composition is a dentifrice, mouthwash or mouthrinse. In certain embodiments the composition is a toothpaste, transparent paste, or gel. In certain embodiments the composition is a paste or gel to be applied to the lips. In certain embodiments the composition is a dentifrice such as a toothpaste or gel.

In certain embodiments, the oral care composition comprises a cationic antibacterial agent. In certain embodiments, the cationic antibacterial agent is chosen from: benzethonium chloride, octenidine, hexetidine, hexamidine, cetyl pyridinium chloride (CPC), alexidine, N.sup..alpha.-acyl amino acid alkyl ester salts (such as ethyl lauroyl arginine ester hydrochloride (ELAH)), and mixtures thereof.

The compositions of the present invention may comprise a fluoride ion source. In certain embodiments, the composition comprises one or more fluoride ion sources, for example soluble fluoride salts. Fluoride sources suitable for use in the present invention may include, but are not limited to: ionic fluorides including alkali metal fluorides; amine fluorides such as olaflur (N'-octadecyltrimethylendiamine-N,N,N'-tris(2-ethanol)-dihydrofluoride), indium fluoride, sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluoride or combinations thereof; and ionic monofluorophosphates including alkali metal monofluorophosphates such as potassium, sodium and ammonium fluoride and monofluorophosphates and mixtures thereof.

In certain embodiments the composition comprises a fluoride ion source selected from one or more of stannous fluoride, sodium fluoride, potassium fluoride, sodium monofluorophosphate, sodium fluorosilicate, ammonium fluorosilicate, amine fluoride, ammonium fluoride and combinations of one or more thereof.

In certain embodiments, the composition comprises sodium monofluorophosphate.

In certain embodiments, the oral care composition of the invention comprises a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts.

In certain embodiments, the composition comprises a fluoride ion source in an amount sufficient to supply about 25 ppm to about 25,000 ppm fluoride ions, for example from about 500 ppm to about 200 ppm, from about 1000 ppm to about 1600 ppm.

In certain embodiments the composition comprises about 0.03 to about 5.0 weight % sodium monofluorophosphate, for example about 0.5 to about 2.0 weight %, from 0.90 to about 1.30 weight %, from about 0.90 to about 1.20 weight % sodium monofluorophosphate or from about 1.00 to about 1.20 weight % sodium monofluorophosphate.

The composition may comprise at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthane glycerol acetal (MGA) and the like. One or more flavorants are optionally present in a total amount of from about 0.01 wt. % to about 5 wt. %, for example, from about 0.1 wt. % to about 2.5 wt. %, by total weight of the composition.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; and combinations thereof. Such agents may be added in effective amounts, e.g., from about 1 wt. % to about 20 wt. % by weight based on the total weight of the composition, depending on the agent chosen.

In certain embodiments the composition may comprise one or more chelating agents. In certain embodiments the composition comprises one or more chelating agent able to complex calcium found in the cell walls of bacteria. In certain embodiments the composition comprises one or more soluble pyrophosphate as chelating agent. In certain embodiments the pyrophosphate salts can be any of the alkali metal pyrophosphate salts. In certain embodiments the salts include tetra alkali metal pyrophosphate, dialkali metal diacid pyrophosphate, trialkali metal monoacid pyrophosphate and mixtures thereof wherein the alkali metals are sodium or potassium. In certain embodiments the composition comprises such pyrophosphate salts in an amount to provide at least about 1 weight % pyrophosphate ions, for example about 1.5 weight % to about 6 weight % or about 3.5 weight % to about 6 weight %.

In certain embodiments the compositions of the invention include one or more polymers such as polyethylene glycols, polyvinylmethyl ether maleic acid copolymers and polysaccharides (e.g. cellulose derivatives such as carboxymethyl cellulose or microcrystalline cellulose, or polysaccharide gums such as xanthan gum or carrageenan gum). Acidic polymers, for example polyacrylate gels, may be provided as free acids or partially or fully neutralized water soluble alkali metal (e.g. potassium and sodium) or ammonium salts.

In certain embodiments the composition comprises about 0.05 to about 5% of an agent which enhances the delivery and retention of oral care agents to and retention thereof on oral surfaces. In certain embodiments the composition comprises synthetic anionic polymeric polycarboxylates such as 1:4 to 4:1 copolymers of maleic anhydride or acid with another polymerizable ethylenically unsaturated monomer, preferably methyl vinyl ether/maleic anhydride having a molecular weight of about 30,000 to about 1,000,000. In certain embodiments the composition comprises from about 0.05 to about 3% by weight of such agents.

In certain embodiments the compositions comprise a thickening material to enhance the performance of the formulation. In certain embodiments the thickening agents are silica, carboxyvinyl polymers, carrageenan, hydroxyethyl cellulose and water soluble salts of cellulose ethers such as sodium carboxy methyl cellulose and sodium carboxymethyl hydroxyethyl cellulose. Natural gums such as karaya, gum arabic and gum tragacanth may also be included. In certain embodiments the composition comprises colloidal magnesium aluminium silicate or finely divided silica. In certain embodiments a thickening agent is present in an amount of about 0.5 to about 5.0%. In certain embodiments the composition comprises from about 0.5 to about 5% cellulose gum. In certain embodiments the composition comprises 1-10 weight % amorphous silica.

In certain embodiments the composition comprises one or more humectants. Humectants can prevent the composition from hardening upon exposure to air. In certain embodiments the composition comprises one or more humectants selected from edible polyhydric alcohols such as glycerine, sorbitol, xylitol, propylene glycol and mixtures thereof. In certain embodiments the composition comprises from about 5 to about 25% humectant. In certain embodiments the composition comprise from about 5 to about 25% glycerine.

In certain embodiments the composition comprises one or more abrasives. In certain embodiments the composition comprises a silica gel or precipitated silica abrasive. In certain embodiments the composition comprises 5 to 30 weight % silica abrasive.

The oral care compositions may comprise at least one sweetener, useful for example to enhance taste of the composition. One or more sweeteners are optionally present in a total amount depending strongly on the particular sweetener(s) selected, but typically 0.005 wt. % to 5 wt. %, by total weight of the composition, optionally 0.01 wt. % to 1 wt. %, further optionally 0.1 wt. % to 0.5 wt. % by total weight of the oral care composition.

The oral care compositions may comprise at least one colorant. Colorants herein include pigments, dyes, lakes and agents imparting a particular luster or reflectivity such as pearling agents. Any orally acceptable colorant can be used. Colorants herein include pigments, dyes, lakes and agents imparting a particular luster or reflectivity such as pearling agents. In certain embodiments, a white colorant is used, for example titanium dioxide ($TiO_2$), titanium dioxide coated mica (e.g., Timiron), a mineral, or a clay. One or more colorants are optionally present in a total amount of from about 0.0001 wt. % to about 5 wt. %, for example, from about 0.0001 wt. % to about 11 wt. %, or from about 0.0005 wt. % to about 0.11 wt. %, by total weight of the oral care composition.

The composition may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention may additionally optionally comprise a tartar control (anticalculus) agent. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers, carboxylate-phosphate copolymers and polyvinyl methyl ether/maleic anhydride (PVM/MA) copolymers, such as GANTREZ®. In certain embodiments the compositions of the present invention comprise 0.1 to 45 weight % tartar control agent. In certain embodiments the compositions of the present invention may comprise 0.1 to 45 weight % polyphosphate, for example 20-30 weight % polyphosphate.

In some embodiments, the compositions of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

The oral compositions may be provided in an orally acceptable carrier or vehicle. The carrier can be a liquid, semi-solid, or solid phase, in the form of a mouth rinse, dentifrice (including toothpastes, toothpowders, and prophylaxis pastes), confectionaries (including lozenges, and gum), medicament, film, or any other form known to one of skill in the art. Selection of specific carrier components is dependent on the desired product form.

Conventional ingredients that can be used to form the carriers listed above are known to the skilled artisan. As recognized by one of skill in the art, the oral compositions optionally include other materials in addition to those components previously described, including for example, surface active agents, emulsifiers, and foam modulators, viscosity modifiers and thickeners, humectants, diluents, additional pH modifying agents, emollients, moisturizers, mouth feel agents, sweetening agents, flavor agents, colorants, preservatives, solvents, such as water and combinations thereof. Any given material may serve multiple purposes within two or more of such categories of materials. Preferably, such carrier materials are selected for compatibility and stability with all of the constituents of the active ingredient, including propolis extract and the one or more oral care active compounds selected for the oral composition.

Typical useful surface active agents are disclosed in the patent references referenced and discussed above, including in U.S. Pat. No. 4,894,220. Surface active agents generally are an important aspect of the oral composition, as they can function as surfactants, emulsifiers foam modulators, and/or active ingredient dispersion agents. Thus, their selection for compatibility with the active ingredient constituents is important. For example, in embodiments where the oral composition has an active ingredient comprising a cationic antibacterial agent, it is preferred that the carrier comprises surfactants that are not strongly anionic, as such anionic compounds can bind to the cationic active ingredient potentially reducing its bioavailability.

Suitable surface active agents are those that are reasonably stable and foam throughout a wide pH range. These compounds are known in the art, and include non-soap anionic (e.g., sodium lauryl sulfate (SLS), N-myristoyl, and N-palmitoyl sarcosine), nonionic (e.g., Polysorbate 20 (polyoxyethylene 20 sorbitan monolaurate, TWEEN® 20) and Polysorbate 80 (polyoxyethylene 20 sorbitan monooleate, TWEEN® 80), Poloxamer 407, available under the trade name Pluronic® F127 from BASF Corporation), cationic, zwitterionic (e.g., cocoamidopropyl betaine and lauramido propyl betaine), and amphoteric organic synthetic detergents. In embodiments where the active ingredient comprises a cationic compound, the surface active agent may be chosen from: non-ionic surfactants, cationic surfactants, betaine surfactants, amphoteric surfactants or mixtures thereof. In various embodiments, one or more surface active agents are present in the oral composition in an amount of about 0.001% to about 5%, or about 0.5% to about 2.5%.

In embodiments where the oral composition is in the form of a mouthrinse or a mouthwash, an exemplary carrier is substantially liquid. The term "mouthrinse" includes mouth washes, sprays, rinses, and the like, in such a preparation the orally acceptable carrier typically has an aqueous phase comprising either water, or a water and alcohol mixture. Further, in various embodiments, the oral carrier typically has a humectant, surfactant, and/or a pH buffering agent.

The compositions of the invention can be used to treat gingivitis and/or periodontitis. Gingivitis and periodontitis are inflammatory conditions of the periodontal tissues of the oral cavity. Gingivitis (inflammation of the gum tissue or gingiva) can be reversed by treatment and good dental hygiene, but if untreated can progress to periodontitis (inflammation of the periodontium). Untreated periodontitis can eventually lead to loss of teeth. The compositions of the invention may be applied to the oral cavity of a subject (in particular to the oral cavity of a human or animal subject) by any means. The application means may vary depending on the formulation of the oral care composition. For example, in certain embodiments the oral care composition is a dentifrice and may be applied to the oral cavity topically using an implement (such as a brush, toothbrush, stick, sponge or cotton swab). In certain embodiments the oral care composition is in the form of a mouthwash or mouthrinse and is applied to the oral cavity by lavage ("swish"). In certain embodiments the oral care composition is applied to surfaces in the oral cavity using a dental tray. In certain embodiments the oral care composition is applied to surfaces in the oral cavity using a dental strip, for example by affixing a strip comprising the oral care composition to the surface of the teeth or gums. In certain embodiments the oral care composition is administered to the oral cavity using an oral care pen. In certain embodiments the oral care composition is applied to the oral cavity at least once or at least twice per day.

The compositions of the invention may include a first feature described in one example herein, as well as a second feature described in another example herein. In other words, the invention contemplates mixing and matching features from the disclosed embodiments in various combinations.

EXAMPLES

Example 1

The antibacterial efficacy of a solution of 0.5 weight % zinc coceth sulfate equivalent to 0.0193 weight % elemental zinc (ZETESOL ZN from Zschimmer & Schwarz supplied as composition with 23.5-25.5% active ZCS) was compared to the antibacterial efficacy of 0.5 weight % sodium lauryl ether sulfate (sodium laureth sulfate or SLES) and an aqueous mix of 1.0 weight % zinc oxide and 0.5 weight % zinc citrate (equivalent to 0.8 wt. % elemental zinc) using a cell viability assay. These compounds were tested in an assay based on the ability of metabolically active bacteria to reduce the blue dye resazurin. A five species mix of representative oral bacterial species was used to simulate the complex bacterial flora of the oral environment. A bacterial mix comprising *Actinomyces viscosus, Lactobacillus casei, Streptococcus oralis, Fusobacteriaum nucleatum* and *Veillonella parvulal* was incubated with the compound under investigation for 1 hour at 37° C., neutralized, washed and stained with 50 µg/ml resazurin solution. When viable bacteria are incubated with resazurin, the blue non-fluorescent dye is reduced by the bacteria to pink fluorescent resorufin. Fluorescence of the test sample is read at 560 nm excitation/590 nm emission and compared to the fluorescence of a standardized mixture of live and dead bacteria to determine the percentage of the initial population that is viable after incubation. The results of this assay are provided in Table 1:

TABLE 1

| Test sample | % bacteria viable following treatment |
|---|---|
| 0.5 wt. % SLES | 19.94 |
| 1.0 wt. % ZnO/0.5 wt. % ZnCitrate | 18.60 |
| 0.5 wt. % ZCS | 10.79 |

The results of this assay demonstrate that zinc coceth sulfate (ZCS) is significantly more efficacious than surfactant alone or an aqueous solution of 0.8 wt. % total elemental zinc.

Example 2

Dentifrice compositions comprising zinc coceth sulfate were prepared and the in vitro antibacterial efficacy of these formulae investigated using a resazurin cell viability assay as described in Example 1. The formulations of these compositions are provided in Table 2.

TABLE 2

| Ingredient (wt. %) | A | B | C | D | Control |
|---|---|---|---|---|---|
| DM water, sweetener, flavoring, colorant | 18.46 | 11.46 | 15.46 | 21.96 | 21.46 |
| Sodium monofluorophosphate | 1.10 | 1.10 | 1.10 | 1.10 | 1.10 |
| Zinc citrate trihydrate | 2.00 | 2.00 | 2.00 | 0.00 | 2.00 |
| Tetrapotassium pyrophosphate | 2.44 | 2.44 | 2.44 | 2.44 | 2.44 |

TABLE 2-continued

| Ingredient (wt. %) | A | B | C | D | Control |
|---|---|---|---|---|---|
| PEG 600 | 3.00 | 3.00 | 3.00 | 3.00 | 3.00 |
| Xanthan Gum | 0.20 | 0.20 | 0.20 | 0.20 | 0.20 |
| Sodium CMC Type 12 | 0.80 | 0.80 | 0.80 | 0.80 | 0.80 |
| Humectant | 34.50 | 34.50 | 34.50 | 34.50 | 34.50 |
| GANTREZ S-97 | 9.10 | 9.10 | 9.10 | 9.10 | 9.10 |
| Sodium hydroxide (50% solution) | 1.40 | 1.40 | 1.40 | 1.40 | 1.40 |
| Syn amorph ppt silica | 10.00 | 10.00 | 10.00 | 10.00 | 10.00 |
| High cleaning silica | 10.00 | 10.00 | 10.00 | 10.00 | 10.00 |
| Syn amorph ppt | 2.00 | 2.00 | 2.00 | 2.00 | 2.00 |
| Zinc coceth sulfate (25% solution) | 4.00 | 12.00 | 8.00 | 2.00 | 0.00 |
| SLS | 1.00 | 0.00 | 0.00 | 1.50 | 2.00 |
| Total elemental zinc | 0.699 | 0.848 | 0.774 | 0.037 | 0.624 |

In order to minimize the effects of formula excipients, dilute 1:100 and 1:10 dentifrice slurries of formulations in water were used in the assay. As before, the test compound (as a dilute slurry) was incubated with the bacteria for 1 hour at 37° C., neutralized, washed and stained with 50 μg/ml resazurin solution. The percentage of viable bacteria was then determined. The results are shown in Table 3.

TABLE 3

| Formula | Zinc source | Total elemental zinc (wt. %) | % bacteria viable following treatment |
|---|---|---|---|
| A | 1% ZCS/2% ZnCitrate | 0.699 | 13.07 |
| B | 3% ZCS/2% ZnCitrate | 0.848 | 41.54 |
| C | 2% ZCS/2% ZnCitrate | 0.774 | 22.59 |
| D | 0.5% ZCS/0% ZnCitrate | 0.037 | 31.56 |
| Control | 2% ZnCitrate | 0.624 | 20.53 |

Further data demonstrating the benefits of ZCS compositions is shown in FIG. 1 in which 0.4% ZCS is equivalent to 0.98% ZnCit, while 1% ZCS is similar to 1.24% ZnCit and 2% ZCS is equivalent to 1% ZCS+1.12% ZnCit. This chart demonstrates that a further increase in ZCS with or without ZnCit appears to perform equally efficaciously. 2% and 3% ZCS with 1.5% SLS appears to do better that other SLS compositions. At 10% treatment dilution there is such severe reduction in bacterial viability that it is not possible to distinguish among test samples. However, treatment with 10% solution of 0.4 and 1% ZCS appears to perform better than ZnCit samples. The formulae containing ZCS at relatively low levels of total zinc give efficacy comparable to 0.8% elemental zinc when delivered from a traditional zinc compound such as zinc citrate. The zinc delivered from ZCS can provide a formula with a high level of in vitro antibacterial efficacy. Thus antibacterial efficacy can be provided whilst avoiding the negative taste implications of existing zinc formulations.

Example 3

A mouthwash composition composing zinc coceth sulfate was prepared as shown Table 4.

TABLE 4

| Ingredient (wt. %) | Mouthwash A |
|---|---|
| DM Water, sweetener, flavoring, coloring | 79.17 |
| Poloxomer 407 | 0.40 |
| CPC | 0.075 |
| Sodium fluoride | 0.05 |
| Zinc Coceth Sulfate, 25% solution | 0.20 |
| Potassium Sorbate | 0.05 |
| Humectants | 20.00 |
| Lactic Acid | 0.053 |

What is claimed is:

1. An oral care composition comprising
zinc coceth sulfate;
wherein the composition comprises an additional zinc ion source comprising zinc citrate;
wherein the zinc coceth sulfate is present at an amount of about 1 weight %;
wherein the oral care composition further comprises sodium lauryl sulfate at an amount of 0.05 weight % to 5.0 weight % relative to the total weight of the oral care composition.

2. The oral care composition of claim 1 further comprising an orally acceptable vehicle.

3. The oral care composition of claim 1 wherein the composition is a dentifrice or mouthwash.

4. The oral care composition of claim 1 wherein the composition further comprises a fluoride ion source.

5. The oral care composition of claim 1 wherein the composition further comprises a non-zinc containing anionic surfactant.

6. The oral care composition of claim 1 wherein the composition further comprises silica.

7. The oral care composition of claim 1 wherein the composition further comprises a polyphosphate.

8. A method of
(i) treating gingivitis and/or periodontitis,
(ii) reducing dental plaque accumulation and/or
(iii) reducing bacteria in the oral cavity of a subject
said method comprising applying a composition according to claim 1 to the oral cavity of a subject.

9. A composition according to claim 1 for use in a method of
(i) treating gingivitis and/or periodontitis,
(i) reducing dental plaque accumulation and/or
(ii) reducing bacteria in the oral cavity of a subject,
said method comprising applying the composition to the oral cavity of a subject.

* * * * *

UNITED STATES PATENT AND TRADEMARK OFFICE
CERTIFICATE OF CORRECTION

PATENT NO. : 10,736,831 B2
APPLICATION NO. : 15/745484
DATED : August 11, 2020
INVENTOR(S) : Kevin Mark Kinscherf et al.

Page 1 of 1

It is certified that error appears in the above-identified patent and that said Letters Patent is hereby corrected as shown below:

In the Specification

In Column 1, Line 50, delete "atones" and insert -- atoms --, therefor.

In Column 6, Line 28, delete "menthane" and insert -- menthone --, therefor.

In Column 7, Line 61, delete "11" and insert -- 1 --, therefor.

In Column 7, Line 62, delete "0.11" and insert -- 0.1 --, therefor.

In Column 9, Line 32, delete "like, in" and insert -- like. In --, therefor.

In Column 10, Line 10, delete "0.0193" and insert -- 0.0393 --, therefor.

In Column 12, Line 5, after "shown", insert -- in --.

In the Claims

In Column 12, Line 52, in Claim 9, delete "(i)" and insert -- (ii) --, therefor.

In Column 12, Line 53, in Claim 9, delete "(ii)" and insert -- (iii) --, therefor.

Signed and Sealed this
Twentieth Day of October, 2020

Andrei Iancu
*Director of the United States Patent and Trademark Office*